United States Patent

Sanchez et al.

[11] Patent Number: 5,981,787
[45] Date of Patent: Nov. 9, 1999

[54] PEROXYOXALATES DERIVED FROM HYDROXY-HYDROPEROXIDES

[75] Inventors: Jose Sanchez, Grand Island, N.Y.; Daryl L. Stein, West Chester, Ohio

[73] Assignee: Elf Atochem North America, Inc., Philadelphia, Pa.

[21] Appl. No.: 08/946,751

[22] Filed: Oct. 10, 1997

Related U.S. Application Data

[60] Provisional application No. 60/034,519, Dec. 30, 1996.

[51] Int. Cl.$^6$ .................................................. C07C 69/96
[52] U.S. Cl. ..................... 558/263; 558/264; 526/230.5; 528/303; 528/491
[58] Field of Search ........................... 560/302; 558/276, 558/263, 264, 203; 526/230.5; 528/303, 491

[56] References Cited

U.S. PATENT DOCUMENTS

| | | | |
|---|---|---|---|
| 3,671,651 | 6/1972 | D'Angelo | 727/323 |
| 3,706,818 | 12/1972 | Mageli et al. | 260/885 |
| 3,853,957 | 12/1974 | D'Angelo et al. | 727/336 |
| 3,893,390 | 7/1975 | D'Angelo et al. | 260/453 |
| 4,525,308 | 6/1985 | Sanchez | 496/357 |
| 4,634,753 | 1/1987 | Sanchez | 717/756 |
| 4,859,794 | 8/1989 | Lundin et al. | 560/302 |

FOREIGN PATENT DOCUMENTS

| | | |
|---|---|---|
| 0049966 A1 | 4/1982 | European Pat. Off. . |
| 0095860 A2 | 7/1983 | European Pat. Off. . |
| 0 500 624 B1 | 5/1991 | European Pat. Off. . |
| 63-248806 | 10/1988 | Japan . |
| 63-254110 | 10/1988 | Japan . |

OTHER PUBLICATIONS

Journal American Chemical Society (82) Apr. 1960 P.D. Bartlett, R. R. Hiatt pp. 1762–1768.
Journal American Chemical Society (82) Dec. 1960 L. S. Silbert & D. Swern pp. 1769–1773.
Journal American Chemical Society (35) Aug. 1970 C. Walling & J. A. McGuinness pp. 1223–1226.
Journal American Chemical Society (99) Mar. 1977 W. Adam & J. Sanabia pp. 2735–2739.
J. Macromol Sci A17(1) Jul. 1982 P. Griffiths, E. Rizzardo, D. Solomon pp. 45–50.
Journal f. prakt. Chemie 324(4) Jun. 1982 J. A. Barth, Leipzig pp. 588–595.

*Primary Examiner*—Samuel Barts
*Attorney, Agent, or Firm*—Stanley A. Marcus; Royal E. Bright

[57] ABSTRACT

Novel peroxyoxalate compositions of Structure A,

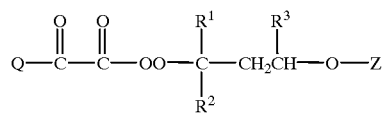

and use of the novel monoperoxyoxalates of Structure A as initiators for polymerizing ethylenically unsaturated monomers and for curing of unsaturated polyester resins are disclosed.

8 Claims, No Drawings

PEROXYOXALATES DERIVED FROM HYDROXY-HYDROPEROXIDES

This Application claims priority from Provisional Application S/N 60/034,519, filed Dec. 30, 1996.

BACKGROUND OF THE INVENTION a) Field of the Invention

This invention relates to compositions classified in the art of chemistry as new and novel peroxyoxalates of Structure A that are preparable by reaction of hydroxy—

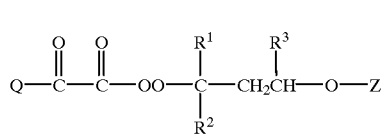

[The definitions of Q, $R^1$, $R^2$, $R^3$ and Z are given in the SUMMARY OF THE INVENTION] hydroperoxides, such as 3-hydroxy-1,1-dimethylbutyl hydroperoxide and 3-hydroxy-1,1-dimethylpropyl hydroperoxide, with oxalyl halides and alkyl halooxalates, such as ethyl chlorooxalate, in the presence or absence of inorganic or organic bases, as well as processes for the preparation and use of the novel peroxyoxalates of Structure A. The peroxyoxalates of Structure A possess inherent applied use characteristics rendering them useful as reaction intermediates and as initiators for polymerizing ethylenically unsaturated monomers and for curing of unsaturated polyester resins.

There is a need in the polymer industries for efficient, free-radical initiators for polymerizing ethylenically unsaturated monomers at lower temperatures in order to attain higher molecular weight polymers having improved tensile and other mechanical properties and/or to increase rates of polymerizations in order to produce current polymers at higher rates of production. In the case of the latter scenario, the more efficient free-radical initiators enable polymer producers to increase productivity without need to build new and expensive production facilities. There also is a need in the polyester industry for free-radical initiators that cure unsaturated polyester resins faster and/or at lower temperatures. The inherent applied use characteristics of the new and novel peroxyoxalate compositions of Structure A of this invention are capable of satisfying these polymer industry needs.

b) Description of the Prior Art

P. D. Bartlett, et al. (*J. Am. Chem. Soc.*, 82, 1762–8, 1960) described the decomposition kinetics of di-t-butyl diperoxyoxalate in solution and found its half-life at 60° C. in benzene to be 6.8 minutes. In a subsequent paper P. D. Bartlett and R. E. Pincock (*J. Am. Chem. Soc.*, 82, 1769–73, 1960) disclosed the decomposition kinetics of di-t-butyl diperoxyoxalate and several OO-t-butyl O-alkyl monoperoxyoxalates including OO-t-butyl O-ethyl monoperoxyoxalate and OO-t-butyl O-benzyl monoperoxyoxalate. Based on the data provided in this reference the 10 Hr half-life temperatures (i.e., the temperature at which 50% of the peroxide is decomposed in 10 hours) were calculated to be 26° C., 39° C. and 41° C., respectively, for the above peroxyoxalates. Thus, di-t-alkyl diperoxyoxalates have 10 Hr half-life temperatures of about 25° C. whereas OO-t-alkyl O-alkyl monoperoxyoxalates have 10 Hr half-life temperatures of about 40° C. An OO-t-alkyl O-alkyl monoperoxyoxalate of the instant invention, i.e., O-ethyl OO-(3-ethoxycarbonylcarbonyloxy-1,1-dimethylbutyl) monoperoxyoxalate (I-1),

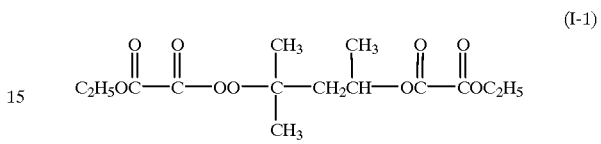

was found to have a 10 Hr half-life temperature of 25° C. in trichloroethylene. Hence, the novel OO-t-alkyl O-alkyl monoperoxyoxalates of the instant invention are significantly more active than the OO-t-alkyl O-alkyl monoperoxyoxalates of the art.

R. A. Sheldon and J. K. Kochi (*J. Org. Chem.*, 35 1223–6, 1970) reported on the rates of decompositions of various di-t-alkyl diperoxyoxalates of the structure,

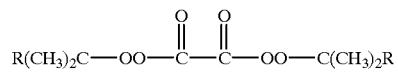

(where R is methyl, ethyl, isopropyl and benzyl)

The data were consistent with those of Bartlett.

W. Adams and J. Sanabia (*J. Am. Chem. Soc.*, 99, 2735–9, 1977) describe the synthesis of a cyclic diperoxyoxalate, 7,7,10,10-tetramethyl-1,2,5,6-tetraoxa-3,4-dioxocyclodecane, from oxalyl chloride and 2,5-dimethyl-2,5-dihydroperoxyhexane in the presence of pyridine. Based on the data provided in this reference the 10 Hr half-life temperature of the cyclic diperoxyoxalate was calculated to be about 80° C.

P. G. Griffiths, et. al. [*J. Macromol. Sci., Chem.*, A17(1), 45–50, 1982] disclose polymerizations of alkyl methacrylates with di-t-butyl diperoxyoxalate (CAS RN 1876-22-2).

European Patent Application No. EP 0049966 A1 (Apr. 21, 1982, to ICI Australia, Ltd.) discloses a process for polymerizing vinyl chloride (VCl) monomer using as an initiator, di-t-butyl diperoxyoxalate.

M. Schulz, et. al. [*J. Prakt. Chem.*, 324(4), 589–95, 1982] describe the synthesis and the thermolysis of azobis(isobutyl t-butyl peroxyoxalate),

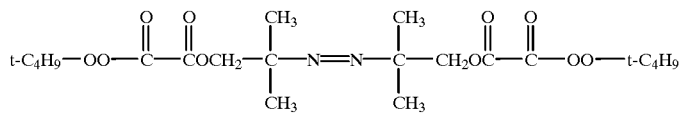

a sequentially decomposing azo-peroxide.

European Patent Application No. EP 0095860 A2 (Dec. 7, 1983, to ICI Australia, Ltd.) discloses a process for polymerizing VCl monomer using as an initiator a diester of monoperoxyoxalic acid of the structure,

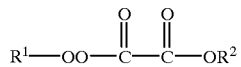

where $R^1$ is a secondary or tertiary alkyl group, or a benzyl or a substituted benzyl group and $R^2$ is a secondary or tertiary alkyl group, or a benzyl or a substituted benzyl group. Also disclosed in this patent application are t-alkylperoxy chlorooxalates of the structure,

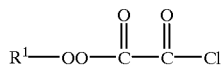

that are used for preparations of the diesters of monoperoxyoxalic acid.

U.S. Pat. No. 4,859,794 (Aug. 22, 1989, to Berol Nobel Nacka AB) discloses dialkyl esters of monoperoxyoxalic acid of structure,

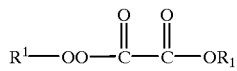

(where $R=C_{4-10}$ t-alkyl and $R_1=C_{18-28}$ primary alkyl) for example, OO-t-butyl O-docosyl monoperoxyoxalate, useful for initiating polymerization of VCl and other monomers.

Japanese Patent Applications JP 63/248806 (Oct. 17, 1988, to NOFCO) and JP 63/254110 (Oct. 20, 1988, to NOFCO) disclose OO-t-alkyl O-alkyl monoperoxyoxalates of the structure,

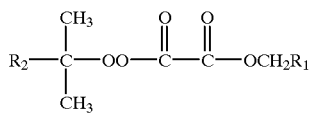

[where $R_1=H$, alkyl and $R_2=C_{1-7}$ alkyl, (substituted) $C_6H_5$, etc.]
as initiators for producing VCl polymers having low odor and color.

European Patent Specification No. 0500624 B1 (Jul. 12, 1994, to Akzo Nobel N.V.) disclosed allyl peroxide chain transfer agents of the structure,

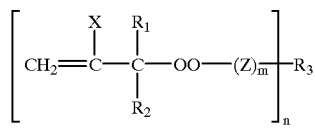

where n is an integer of 1–4, $R_1$ and $R_2$ may be the same or different and are selected from hydrogen or lower alkyl, $R_3$ is selected from alkyl of 4–8 carbons, alkenyl of 5–18 carbons, etc., X is an activating group capable of enhancing the reactivity of the olefinic unsaturation towards free-radical addition, m is 0 or 1 and Z is selected from the structures,

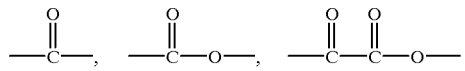

If Z is the latter structure then the compounds of European Patent Specification No. 0500624 B1 can be monoperoxyoxalates. However, the compositions of 0500624 B1 do not disclose the compositions of the instant invention since the peroxides of Structure A are not allyl peroxides nor does the instant invention cover the compositions of 0500624 $B_1$. It should be noted that no monoperoxyoxalates are included in the list of peroxides on pages 5, 7 and 8 or in the preparative examples of 0500624 B1.

As a whole, the above art does not disclose OO-t-alkyl O-alkyl peroxyoxalates which possess hydroxy, chlorocarbonyl-carbonyloxy, carboxycarbonyloxy or alkoxycarbonylcarbonyloxy groups on the OO-t-alkyl group such as in Structure A.

U.S. Pat. No. 3,236,872 (Feb. 22, 1966, to Laporte Chemical, Ltd.) discloses hydroxy-peroxides of the structure:

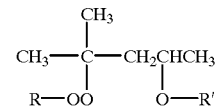

(wherein R is a H, an acyl, an aroyl or alkyl group, especially the t-butyl group, t-amyl or the hexylene glycol residue; R' is an H or an acyl, aroyl or alkyl group.)

U.S. Pat. No. 4,525,308 (Jun. 25, 1985, to Pennwalt Corp.) and U.S. Pat. No. 4,634,753 (Jan. 6, 1987, to Pennwalt Corp.) disclose hydroxy-peroxyesters (above structure where R' is H and R is an acyl group) having 10 hour half-life temperatures below about 75° C.

U.S. Pat. No. 3,853,957 (Dec. 10, 1974, to Pennwalt Corp.) discloses diperoxyketals and ketone peroxides containing hydroxy and acyloxy groups.

U.S. Pat. No. 3,671,651 (Jun. 20, 1972, to Pennwalt Corp.) discloses a hydroxy-peroxyester, t-butyl peroxy-3-hydroxypropionate, however, the product was difficult to prepare and, in addition, the substrate employed in the synthesis, i.e., β-propiolactone, is a highly toxic cancer suspect agent.

U.S. Pat. No. 3,706,818 (Dec. 19, 1972, to Pennwalt Corp.) and U.S. Pat. No. 3,839,390 (Oct. 1, 1974, to Pennwalt Corp.) disclose sequential polyperoxides possessing peroxide moieties of differing structures and activities in the same molecule. The structures of this art do not anticipate the novel peroxyoxalates of Structure A.

c) Definitions

The 10 Hr half-life temperature of a free-radical initiator (e.g., an organic peroxide) is defined as the temperature at which half (50%) of the initiator decomposes in 10 hours.

In the instant invention, the monoperoxyoxalic acid, alkyl, t-alkyl esters Z,

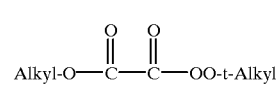

are named OO-t-alkyl O-alkyl monoperoxyoxalates. t-Cycloalkyl refers to the monoradical structure,

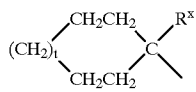

where t is 0 to 2 and $R^x$ is a lower alkyl radical of 1 to 4 carbons, t-alkynyl is the monoradical structure,

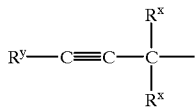

where $R^y$ is hydrogen or a lower alkyl radical of 1 to 4 carbons, and t-aralkyl is the monoradical structure,

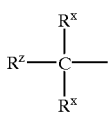

where $R^z$ is an aryl radical of 6 to 10 carbons.

When any generalized functional group or index, such as R, $R^1$, $R^2$, x, n, etc., appears more than once in a general formula or structure, the meaning of each is independent of one another.

SUMMARY OF THE INVENTION

The invention provides in a composition aspect a peroxyoxalate of Structure A:

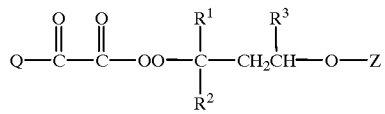

where $R^1$, $R^2$ and $R^3$ are alkyl radicals of 1 to 4 carbons, and, additionally, $R^3$ can be hydrogen, and, Q is selected from the group consisting of chloro, bromo, R—O, and $R^4$—OO, where R is selected from the group consisting of H, a substituted or unsubstituted alkyl radical of 1 to 24 carbons, substituents being one or more alkyl radicals of 1 to 6 carbons, alkoxy radicals of 1 to 6 carbons, aryloxy radicals of 6 to 10 carbons, fluoro, chloro, bromo, carboxy and cyano, a substituted or unsubstituted alkenyl radical of 3 to 12 carbons, substituents being one or more lower alkyl radicals of 1 to 4 carbons, a substituted or unsubstituted aryl radical of 6 to 10 carbons, substituents being one or more alkyl radicals of 1 to 6 carbons, alkoxy radicals of 1 to 6 carbons, aryloxy radicals of 6 to 10 carbons, chloro, bromo and cyano, a substituted or unsubstituted aralkyl radical of 7 to 13 carbons, substituents being one or more alkyl radicals of 1 to 6 carbons, a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, a substituted or unsubstituted bicycloalkyl radical of 6 to 14 carbons, with substituents being one or more lower alkyl radicals of 1 to 4 carbons, and, R- can additionally be structure (a),

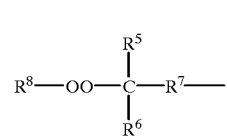

where $R^5$ and $R^6$ are alkyl radicals of 1 to 4 carbons, $R^7$ is an unsubstituted alkylene diradical of 1 to 3 carbons or a substituted alkylene diradical of 1 to 3 carbons, substituents being one or more lower alkyl radicals of 1 to 4 carbons, $R^8$ is selected from unsubstituted t-alkyl radicals of 4 to 12 carbons, substituted t-alkyl radicals of 4 to 12 carbons, t-cycloalkyl radicals of 6 to 13 carbons, t-alkynyl radicals of 5 to 9 carbons, t-aralkyl radicals of 9 to 13 carbons, unsubstituted aroyl radicals of 7 to 11 carbons, substituted aroyl radicals of 7 to 11 carbons, where the substituent for the t-alkyl radicals is a t-alkylperoxy radical of 4 to 8 carbons and the substituents for the aroyl radicals are one or more lower alkyl radicals of 1 to 4 carbons, alkoxy radicals of 1 to 4 carbons, phenyl radicals, acyloxy radicals of 2 to 8 carbons, t-alkylperoxycarbonyl radicals of 5 to 9 carbons, fluoro, chloro or bromo, and $R^8$ can also be structures (b), (c) and (d)

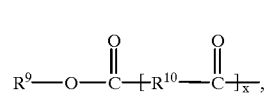

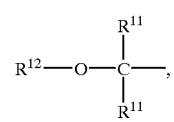

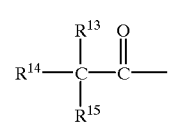

where x is 0 or 1, $R^9$ is a substituted or unsubstituted alkyl radical of 1 to 18 carbons, substituents being one or more alkyl radicals of 1 to 6 carbons, t-alkylperoxy radicals of 4 to 8 carbons, alkoxy radicals of 1 to 6 carbons, aryloxy radicals of 6–10 carbons, hydroxy, chloro, bromo or cyano or a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, and, $R^{10}$ is selected from a substituted or unsubstituted alkylene diradical of 2 to 3 carbons, substituents being one or more lower alkyl radicals of 1 to 4 carbons, or a substituted or unsubstituted 1,2-, 1,3- or 1,4-phenylene diradical, substituents being one or more lower alkyl radicals of 1 to 4 carbons, chloro, bromo, nitro or carboxy, and, $R^{11}$ is a lower alkyl radical of 1 to 4 carbons, and, additionally, the two $R^{11}$ radicals may be concatenated to form an alkylene diradical of 4 to 5 carbons, $R^{12}$ is a lower alkyl radical of 1 to 4 carbons, $R^{13}$, $R^{14}$ and $R^{15}$ are selected from hydrogens, alkyl radicals of 1 to 8 carbons, aryl radicals of 6 to 10 carbons, alkoxy radicals of 1 to 8 carbons and aryloxy radicals of 6 to 10 carbons, and, $R^4$ is selected from an unsubstituted t-alkyl radical of 4 to 12 carbons, a substituted t-alkyl radical of 4 to 12 carbons, a t-cycloalkyl radical of 6 to 13 carbons, a t-alkynyl radical of 5 to 9 carbons, and a t-aralkyl radical of 9 to 13 carbons, where the substituent for the t-alkyl radical is a t-alkylperoxy radical of 4 to 8 carbons, preferably, R is selected from the group consisting of H, a substituted or unsubstituted alkyl radical of 1 to 18 carbons, substituents being one or more alkyl radicals of 1 to 6 carbons, alkoxy radicals of 1 to 6 carbons, aryloxy radicals of 6 to 10 carbons, fluoro, chloro, bromo, carboxy and cyano, a substituted or unsubstituted aralkyl radical of 7 to 13 carbons, substituents being one or more alkyl radicals of 1 to 6 carbons, a substituted or unsubstituted cycloalkyl radical of 5 to 12 carbons, substituents being one or more lower alkyl radicals of 1 to 4 carbons, and structure (a), more preferably, R is selected from the group consisting of H, a substituted or unsubstituted alkyl radical of 1 to 18 carbons, substituents being one or more alkyl radicals of 1 to 6 carbons, alkoxy radicals of 1 to 6 carbons, aryloxy radicals of 6 to 10 carbons, fluoro, chloro, bromo, carboxy and cyano, a substituted or unsubstituted cycloalkyl radical of 5 to 12 carbons, substituents being one or more lower alkyl radicals of 1 to 4 carbons, and structure (a), and, Z is selected from the group consisting of hydrogen and structures (e), (f) and (g),

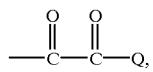
(e)

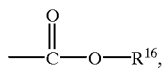
(f)

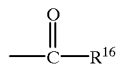
(g)

where $R^{16}$ is selected from the group consisting of a substituted or unsubstituted alkyl radical of 1 to 24 carbons, substituents being one or more alkyl radicals of 1 to 6 carbons, alkoxy radicals of 1 to 6 carbons, aryloxy radicals of 6 to 10 carbons, chloro, bromo, carboxy and cyano, a substituted or unsubstituted alkenyl radical of 3 to 12 carbons, substituents being one or more lower alkyl radicals of 1 to 4 carbons, a substituted or unsubstituted aryl radical of 6 to 10 carbons, substituents being one or more alkyl radicals of 1 to 6 carbons, alkoxy radicals of 1 to 6 carbons, aryloxy radicals of 6 to 10 carbons, chloro, bromo and cyano, a substituted or unsubstituted aralkyl radical of 7 to 13 carbons, substituents being one or more alkyl radicals of 1 to 6 carbons, a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, and a substituted or unsubstituted bicycloalkyl radical of 6 to 10 carbons, with substituents being one or more lower alkyl radicals of 1 to 4 carbons, preferably, Z is hydrogen or structure (e), more preferably, Z is structure (e).

The invention provides in a process aspect, a process for the free radical induced addition of unsaturated substrates selected from the group consisting of:

Processes using a peroxide composition of Structure A as a curing agent for the free radical curing of unsaturated polyester resin compositions by heating such resins in the presence of initiating amounts of the peroxide composition of Structure A at appropriate temperatures, and, Processes using a peroxide composition of Structure A as a free-radical initiator for polymerizing ethylenically unsaturated monomers (such as styrene, ethylene etc.) by the use of initiating amounts of the peroxide composition of Structure A at appropriate temperatures.

DETAILED DESCRIPTION OF THE PREFERRED EMBODIMENTS

Peroxyoxalate Compositions of Structure A—Preparative Methods

The novel peroxyoxalate compositions of Structure A may be prepared by reacting hydroxy-hydroperoxides of Structure B,

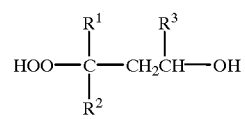
B with oxalyl halides, alkyl halooxalates or t-alkylperoxy halooxalates of Structure C,

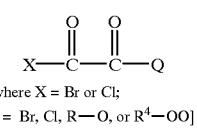
C

[where X = Br or Cl;
Q = Br, Cl, R—O, or $R^4$—OO]

at −90° C. to 50° C., optionally in the presence of an inorganic or organic base, and optionally in the presence one or more solvents. The compositions of Structure C are oxalyl halides, e.g., oxalyl bromide and oxalyl chloride, when X and Q are Br and Cl. The compositions of Structure C are alkyl halooxalates when X is Br or Cl and Q is R—O. The compositions of Structure C are t-alkylperoxy halooxalates when X is Br or Cl and Q is $R^4$—OO.

Non-limiting examples of suitable optional solvents include pentane, hexanes, heptanes, dodecanes, odorless mineral spirits mixtures, toluene, xylenes, cumene, methylene chloride, ethyl acetate, 2-ethylhexyl acetate, isobutyl isobutyrate, dimethyl adipate, dimethyl succinate, dimethyl glutarate (or mixtures thereof), dimethyl phthalate, dibutyl phthalate, benzyl butyl phthalate, diethyl ether, methyl t-butyl ether, 2-methoxyethyl acetate and others.

Non-limiting examples of suitable optional bases include triethylamine, tributylamine, N,N-diisopropylethylamine, 2,2,6,6-tetramethylpiperidine, N,N-dimethylaniline, N,N-dimethylaminopyridine, 2,4,6-colidine, urea, tetramethylurea, sodium hydroxide, sodium carbonate, sodium hydrogen carbonate, potassium hydroxide, potassium carbonate, potassium hydrogen carbonate, calcium hydroxide, magnesium hydroxide, barium hydroxide, calcium carbonate and trisodium phosphate.

Non-limiting examples of suitable hydroxyhydroperoxides of Structure B that can be reacted with alkyl halooxalates of Structure C include 3-hydroxy-1,1-dimethylpropyl hydroperoxide and 3-hydroxy-1,1-dimethylbutyl hydroperoxide.

Non-limiting examples of suitable oxalyl halides include oxalyl bromide and oxalyl chloride. Non-limiting examples of suitable alkyl halooxalates of Structure C (X=Br or Cl; Q=R—O) that can be reacted with hydroxy-hydroperoxides of Structure B include ethyl bromooxalate, methyl chlorooxalate, ethyl chlorooxalate, n-butyl chlorooxalate, t-butyl chlorooxalate, 2-ethylhexyl chlorooxalate, dodecyl chlorooxalate, docosyl chlorooxalate, hexafluoroamyl chlorooxalate, allyl chlorooxalate, phenyl chlorooxalate, 2-phenoxyethyl chlorooxalate, cyclohexyl chlorooxalate, 4-t-butylcyclohexyl chlorooxalate, isobornyl chlorooxalate, bornyl chlorooxalate, benzyl chlorooxalate, 3-t-butylperoxy-1,3-dimethylbutyl chlorooxalate and 3-(2-ethylhexanoylperoxy)-1,3-dimethylbutyl chlorooxalate. The above alkyl halooxalates can be prepared by reacting 0 to 100% excess oxalyl bromide or oxalyl chloride with the corresponding alkanol until the reaction is completed. The excess oxalyl halide is removed by stripping or by distillation. Non-limiting examples of suitable alkanols that react with oxalyl halides to form alkyl halooxalates of Structure C include methanol, ethanol, n-butanol, t-butanol, 2-ethylhexanol, dodecanol, docosanol, hexafluoroamyl alcohol, allyl alcohol, cyclohexanol, 4-t-butylcyclohexanol, menthol, isoborneol, borneol, phenol, 2-phenoxyethanol, benzyl alcohol, 3-t-butylperoxy-1,3-dimethylbutanol and 3-hydroxy-1,1-dimethylbutyl 2-ethylperoxyhexanoate.

Non-limiting examples of suitable t-alkylperoxy halooxalates of Structure C (X=Br or Cl; Q=R$^4$—OO) that can be reacted with hydroxy-hydroperoxides of Structure B include t-butylperoxy chlorooxalate, t-amylperoxy chlorooxalate, 1,1,3,3-tetramethylbutylperoxy chlorooxalate, and isopropyl-α-cumylperoxy chlorooxalate. The t-alkylperoxy halooxalates of Structure C can be prepared by reacting excess oxalyl halides, e.g., oxalyl bromide and oxalyl chloride, with t-alkyl hydroperoxides, optionally in the presence one or more solvents. The excess oxalyl halide and optional solvents can be removed from the t-alkylperoxy halooxalates by stripping or by distillation. Non-limiting examples of suitable optional solvents are given above. Non-limiting examples of suitable t-alkyl hydroperoxides for preparing the t-alkylperoxy halooxalates of Structure C include t-butyl hydroperoxide, t-amyl hydroperoxide, t-hexyl hydroperoxide, 1,1,3,3-tetramethylbutyl hydroperoxide, 1-methylcyclohexyl hydroperoxide, para-menthane hydroperoxide, 2-hydroperoxy-2-methyl-3-butyne, α-cumyl hydroperoxide, and diisopropylbenzene monohydroperoxide.

Novel O-alkyl OO-(hydroxy-t-alkyl) peroxyoxalates of Structure D that can be prepared by the synthetic processes of this

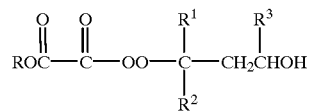

invention can be further reacted with alkyl halooxalates (or oxalyl halides or t-alkylperoxy halooxalates), alkyl haloformates and carboxylic acid halides (or carboxylic acid anhydrides), optionally in the presence of an inorganic or organic base, and optionally in the presence of a solvent, to form novel monoperoxyoxalates of Structure A where Z is structure (e), (f) and (g), respectively. Non-limiting examples of suitable oxalyl halides, alkyl halooxalates, inorganic or organic bases and optional solvents are listed above. Non-limiting examples of suitable alkyl haloformates include isopropyl bromoformate, methyl chloroformate, cyclohexyl chloroformate, 4-t-butylcyclohexyl chloroformate, 2-phenoxyethyl chloroformate, 3-t-butylperoxy-1,3-dimethylbutyl chloroformate, phenyl chloroformate and benzyl chloroformate. Non-limiting examples of suitable carboxylic acid halides or carboxylic acid anhydrides include acetyl chloride, benzoyl chloride, isobutyryl chloride, lauroyl chloride, pivaloyl chloride, neodecanoyl chloride, acetic anhydride, propionic anhydride and succinic anhydride.

Novel peroxyoxalates of Structure E can be prepared

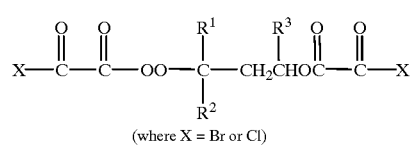

by reacting hydroxy-hydroperoxides with excess oxalyl halides such as oxalyl bromide and oxalyl chloride. The novel peroxyoxalates of Structure E provide substrates for alternate synthetic routes to some of the novel monoperoxyoxalates of Structure A. For example, the monoperoxyoxalates of Structure E can be further reacted with excess water, alkanols or excess t-alkyl hydroperoxides, in the presence of an inorganic or organic base, and optionally in the presence of a solvent, to produce novel peroxyoxalates of Structure F.

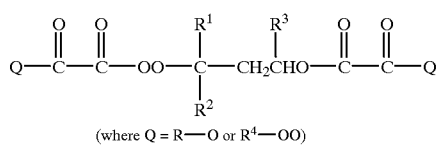

Non-limiting examples of suitable inorganic or organic bases, optional solvents, alkanols and t-alkyl hydroperoxides are listed above.

Novel Peroxyoxalate Compositions of Structure A—Illustrative Examples

Non-limiting examples of the novel peroxyoxalates of Structure A, in addition to those in the teaching examples, include the following:

1-methyl-3-(chlorocarbonylcarbonylperoxy)butyl chlorooxalate, O-methyl OO-(3-hydroxy-1,1- dimethylpropyl) monoperoxyoxalate, O-cyclohexyl OO-(3-hydroxy-1,1-dimethylbutyl) monoperoxyoxalate, O-octyl OO-(3-hydroxy-1,1-dimethylbutyl) monoperoxyoxalate, O-dodecyl OO-(3-hydroxy-1,1-dimethylbutyl) monoperoxyoxalate, O-(4-t-butylcyclohexyl) OO-(3-hydroxy-1,1-dimethylbutyl) monoperoxyoxalate, O-(2-phenoxyethyl) OO-(3-hydroxy-1,1-dimethylbutyl) monoperoxyoxalate, O-allyl OO-(3-hydroxy-1,1-dimethylbutyl) monoperoxyoxalate, O-phenyl OO-(3-hydroxy-1,1-dimethylbutyl) monoperoxyoxalate, O-benzyl OO-(3-hydroxy-1,1-dimethylbutyl) monoperoxyoxalate, O-(3-t-butylperoxy-1,1-dimethylbutyl) OO-(3-hydroxy-1,1-dimethylbutyl) monoperoxyoxalate, O-methyl OO-(3-methoxycarbonylcarbonyloxy-1,1-dimethylbutyl) monoperoxyoxalate, O-cyclohexyl OO-(3-cyclohexoxycarbonylcarbonyloxy-1,1-dimethylbutyl) monoperoxyoxalate, O-bornyl OO-(3-bornyloxycarbonylcarbonyloxy-1,1-dimethylbutyl) monoperoxyoxalate, O-butyl OO-(3-butoxycarbonylcarbonyloxy-1,1-dimethylbutyl) monoperoxyoxalate, O-octyl OO-(3-octoxycarbonylcarbonyloxy-1,1-dimethylbutyl) monoperoxyoxalate, O-(2-ethylhexyl) OO-[3-(2-ethylhexoxycarbonylcarbonyloxy)-1,1-dimethylbutyl] monoperoxyoxalate, O-(4-t-butylcyclohexyl) OO-[3-(4-t-butylcyclohexoxycarbonylcarbonyloxy)-1,1-dimethylbutyl] monoperoxyoxalate, O-phenyl OO-(3-phenoxycarbonylcarbonyloxy-1,1-dimethylbutyl) monoperoxyoxalate, O-benzyl OO-(3-benzyloxycarbonylcarbonyloxy-1,1-dimethylbutyl) monoperoxyoxalate, O-(2-phenoxyethyl) OO-[3-(2-phenoxyethoxycarbonylcarbonyloxy)-1,1-dimethylbutyl] monoperoxyoxalate and O-allyl OO-(3-allyloxycarbonylcarbonyloxy-1,1-dimethylbutyl) monoperoxyoxalate, O-cyclohexyl OO-(3-methoxycarbonyloxy-1,1-dimethylbutyl) monoperoxyoxalate, O-cyclohexyl OO-(3-ethoxycarbonyloxy-1,1-dimethylbutyl) monoperoxyoxalate, O-(2-ethylhexyl) OO-(3-acetoxy-1,1-dimethylbutyl) monoperoxyoxalate, t-butyl 3-t-butylperoxycarbonylcarbonyloxy-1,1-dimethylpropyl diperoxyoxalate, and t-amyl 3-t-amylperoxycarbonylcarbonyloxy-1,1-dimethylbutyl diperoxyoxalate.

Novel Peroxyoxalate Compositions of Structure A—Utility

A. Polymerization of Ethylenically Unsaturated Monomers

In the free-radical polymerizations of ethylenically unsaturated monomers at suitable temperatures and pressures the novel peroxyoxalate compositions of Structure A of this invention were found to be effective initiators with respect to efficiency (reduced initiator requirements, etc.). Ethylenically unsaturated monomers include olefins, such as ethylene, propylene, styrene, alpha-methylstyrene, p-methylstyrene, chlorostyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, allyl, methyl, ethyl, n-butyl, 2-hydroxyethyl, glycidyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate diethylene glycol bis(allyl carbonate) (i.e., ADC); acrolein; methyl vinyl ketone; or mixtures thereof.

Temperatures of 0° C. to 100° C., preferably 20° C. to 90° C., more preferably 30° C. to 75° C. and levels of peroxyoxalates of Structure A (on a pure basis) of 0.002 to 10% or more, preferably 0.005% to 2%, more preferably 0.01% to 1% by weight based on monomer, are normally employed in conventional polymerizations and copolymerizations of ethylenically unsaturated monomers. The novel peroxide compositions of this invention can be used in combination with other free-radical initiators such as those disclosed at the bottom of column 4 and the top of column 5 of U.S. Pat. No. 4,525,308. Using the peroxide compositions of this invention in combination with these initiators adds flexibility to the processes of polymer producers and permits them to "fine tune" their polymerization processes.

B. Curing of Unsaturated Polyester Resins

In the curing of unsaturated resin compositions by heating at suitable curing temperatures in the presence of free-radical curing agents, the novel peroxyoxalate compositions of Structure A of this invention exhibit enhanced curing activity in the curable unsaturated polyester resin compositions. Unsaturated polyester resins that can be cured by the novel peroxyoxalate compositions of this invention usually include an unsaturated polyester and one or more ethylenically unsaturated monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxymethyl-2-methyl-1,3-propanediol, 2-buten-1,4-diol, 2-butyn-1,4-diol, 2,4,4-trimethyl-1,3-pentanediol, glycerol, pentaerythritol, mannitol and others. Mixtures of such di- or polyacids and/or mixtures of such di- or polyols may also be used. The di- or polycarboxylic acids may be partially replaced by saturated di- or polycarboxylic acids, such as adipic acid, succinic acid, sebacic acid and other, and/or by aromatic di- or polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, tetrabromophthalic acid, 5,6-dicarboxy-1,2,3,4,7,7-hexachlorobicyclo(2.2.1)-2-heptene and others.

The other component of the unsaturated polyester resin composition, the polymerizable monomer or monomers, can preferably be ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and others, or mixtures thereof, which are copolymerizable with said unsaturated polyesters.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid) as well as the monomer component, styrene.

Other types of unsaturated polyester resin compositions can be cured using the novel peroxide compositions of this invention as curing catalysts. These resins, called unsaturated vinyl ester resins, consist of a vinyl ester resin portion and one or more polymerizable monomer components. The vinyl ester resin component can be made by reacting a chloroepoxide, such as epichlorohydrin, with appropriate amounts of a bisphenol such as Bisphenol A [2,2-(4-hydroxyphenyl)propane], in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to 200° C. and levels of novel peroxyoxalates of Structure A of about 0.05% to 5% or more, preferably 0.10% to 4%, more preferably 0.25% to 3% by weight of curable unsaturated polyester resin composition are normally employed.

The unsaturated polyester resin compositions described above can be filled with various materials, such as sulfur, glass, carbon and boron fibers, carbon blacks, silicas, metal silicates, clays, metal carbonates, antioxidants (AO's), heat, ultraviolet (UV) and light stabilizers, sensitizers, dyes, pigments, accelerators, metal oxides, such as zinc oxide, blowing agents, nucleating agents and others.

C. Curing of Allyl Diglycol Carbonate (ADC) Resins

In the curing or polymerizing of diethylene glycol bis (allyl carbonate) (ADC),

ADC by heating ADC monomer at suitable curing temperatures in the presence of free-radical curing agents, the novel peroxyoxalate compositions of Structure A of this invention exhibit enhanced curing or polymerizing activity for ADC monomer compositions. ADC was introduced commercially as CR-39 monomer (CAS Reg. No. 142-22-3) by Pittsburgh Plate Glass Company (PPG) and is produced by reacting diethylene glycol bis(chloroformate) with allyl alcohol in the presence of alkali (R. Dowbenko, in J. I. Kroschwitz and M. Howe-Grant, eds., *Kirk-Othmer—Encyclopedia of Chemical Technology*, "Allyl Monomers and Polymers," Fourth Edition, Vol. 2, Wiley-Interscience Publication, John Wiley & Sons, Inc., New York, 1992, pp 163–168). The ADC monomer can cured or polymerized alone or with other co-monomers such as such as acrylic acid esters, methacrylic acid esters, allyl esters, diallyl dicarboxylates (e.g., diallyl phthalate), maleic anhydride and other monomers to produce clear castings or lenses that are transparent, tough, break-resistant and solvent-resistant. Curing or polymerizing of ADC monomer compositions are carried out in bulk (no solvent present). In general, curing or polymerizing of ADC monomer compositions to form cast sheets or lenses is carried out in two stages. The first stage involves the major part of the polymerization and occurs in the presence of the curing initiator, usually a lower dialkyl peroxydicarbonate, at temperatures of 35° C. to 120° C. Curing or polymerization times vary from about 5 hours to 50 hours. Generally a time-temperature profile is employed in the first stage. An example of a time-temperature profile is given below:

TYPICAL CURE TEMPERATURE SCHEDULE
FOR CURING OF ADC

| TYPICAL CURE TEMPERATURE SCHEDULE FOR CURING OF ADC | |
|---|---|
| TIME (HOURS) | TEMPERATURE (° C.) |
| 0.0 | 61 |
| 1.0 | 62 |
| 3.0 | 64 |
| 7.0 | 68 |
| 8.0 | 69 |
| 8.5 | 74 |
| 9.0 | 79 |
| 9.5 | 86.5 |
| 10.0 | 96.5 |
| 10.5 | 115 |
| 10.75 | 85 |
| 11.0 | 60 |
| 11.25 | 40 |
| 11.5 | 30 |

The second stage of the curing or polymerizing of ADC monomer compositions involves post-curing or annealing of the ADC resin for one to several hours at 100° C. to 150° C. An example of post-curing of the ADC resin would be 2 hours at 115° C.

Levels of the novel peroxyoxalate compositions of about 1% to 6% or more, preferably 2% to 5%, more preferably 2.5% to 4% by weight of curable or polymerizable ADC monomer composition, are normally employed.

The ADC resin compositions described above can be filled with various materials, such as antioxidants (AO's), heat, ultraviolet (UV) and light stabilizers, tints, photochromic additives and dyes. In addition, the ADC resin compositions can contain additives such as acrylic polymers and the anti-shrink, low molecular weight acrylic resins disclosed in U.S. Pat. No. 4,217,433. Such anti-shrink additives are employed to counter the 14% shrinkage that occurs when ADC monomer is polymerized.

Novel Peroxyoxalate Compositions of Structure
A—Preparative and Utility Examples The following examples further illustrate the best mode contemplated by the inventors for practicing the instant invention, and are presented to provide detailed preparative and utility illustrations of the invention and are not intended to limit the breadth and scope of the invention.

EXAMPLE 1

Preparation of O-Ethyl OO-(3-Ethoxycarbonylcarbonyloxy-1,1-dimethylbutyl) Monoperoxyoxalate (I-1)

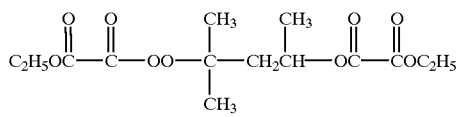

(I-1)

A 250 mL 3-necked flask equipped with a magnetic stirring bar, a condenser, a thermometer and an addition funnel and cooled with an ice bath was charged with 4.3 g (30.0 mmoles) of dry 94.4% 3-hydroxy-1,1-dimethylbutyl hydroperoxide, 6.7 g (85.0 mmoles) of dry pyridine and 60 mL of methyl t-butyl ether (MTBE). The flask contents were cooled to 1° C. Then to the resulting vigorously stirred solution at 5–8° C. was slowly added a solution of 8.8 g (63.0 mmoles) of 98% ethyl oxalyl chloride in 10 mL of MTBE. A solid, pyridinium chloride, formed shortly after the addition commenced. After the addition was completed the reaction mass was stirred for 45 minutes at 2° C. after which 10 mL of water was added and the reaction mass was stirred an additional 20 minutes at 3–4° C. The aqueous layer was then separated and the organic layer was washed three times with 35 mL portions of aqueous 5% HCl solution and then twice with 75 mL portions of water. The product solution was dried over 5% by weight of anhydrous $MgSO_4$, and, after separation of the spent desiccant by filtration, the solvent was removed in vacuo leaving 11.3 g (>100% of theory, uncorrected) of a colorless liquid. An infrared (IR) spectrum of the product showed a slight OH band in the 3500 $cm^{-1}$ region. A major monoperoxyoxalate carbonyl band was present at 1791.1 $cm^{-1}$, a major oxalate carbonyl band was present at 1741.6 $cm^{-1}$ and a peroxide (—OO—) band was present at about 860 $cm^{-1}$. The product had a rapid heat test [J. Chem. Ed. 48, A451 (1970)] result of 62° C. which confirmed that the product was a very low temperature peroxide. The product contained 4.77% active oxygen (theory, 4.79%) according to a peroxyester active oxygen method, therefore, the assay of the product was 99.6% and the corrected yield was 100%.

Based on the method of preparation, yield data, rapid heat data and infrared spectral data the product obtained in this reaction was the desired title product.

O-Ethyl OO-(3-ethoxycarbonylcarbonyloxy-1,1-dimethylbutyl) monoperoxyoxalate (I-1) was found to have a 10 Hr half-life temperature of 25° C. in trichloroethylene, therefore, I-1 was an extremely active peroxide compared to the OO-t-alkyl O-alkyl monoperoxyoxalates of the art.

EXAMPLE 2

Preparation of 1,3-Dimethyl-3-(chlorocarbonylcarbonylperoxy)butyl Chlorooxalate (I-2)

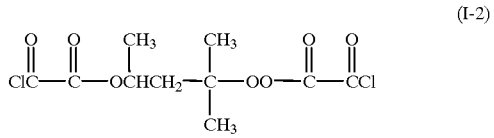

(I-2)

A 250 mL 3-necked flask equipped with a magnetic stirring bar, a condenser, a thermometer and an addition funnel and cooled with an ice bath was charged with 38.1 g (300 mmoles) of oxalyl chloride and 80 mL of MTBE. The flask contents were then cooled to 1° C. Then 4.3 g (30 mmoles) of dry 94.4% 3-hydroxy-1,1-dimethylbutyl hydroperoxide and 9.5 g of methoxyethyl ether (diglyme) in 20 mL of MTBE were slowly added to the the flask contents over a period of 30 minutes at 1° C. The diglyme was employed as a safety diluent for the product. Then the reaction mass was further stirred for 120 minutes at 0° C. after which the MTBE and excess oxalyl chloride were removed in vacuo using a water aspirator at 0° C. leaving 23.5 g (>100% of theory, uncorrected; expected yield=19 g of diglyme diluted product) of a slightly yellow liquid. An IR spectrum of the product showed only a trace of an OH band in the 3500 $cm^{-1}$ region. A major monoperoxyoxalate carbonyl band was present at 1790 $cm^{-1}$ and a major oxalate carbonyl band was present at about 1750 $cm^{-1}$. The product had a rapid heat test result of 66° C. which confirmed that the product was a very low temperature peroxide.

Based on the method of preparation, crude yield data, rapid heat data and infrared spectral data the product obtained in this reaction was the desired title product.

A second preparation of the title peroxide was carried out in a similar manner except that only 4.0 g of diglyme safety diluent was employed. In this experiment 16.8 g (>100% of theory, uncorrected; expected yield=13.5 g of diglyme diluted product) of a slightly yellow liquid product was obtained. An IR spectrum of the product showed only a trace of an OH band in the 3500 $cm^{-1}$ region. A major monoperoxyoxalate carbonyl band was present at 1795 $cm^{-1}$ and a major oxalate carbonyl band was present at about 1750 $cm^{-1}$. The product had a rapid heat test result of 63° C. (loud pop) which again confirmed that the product was a very low temperature peroxide.

The desired peroxide product was prepared in this experiment based on the method of preparation, crude yield data, rapid heat data and infrared spectral data that were obtained.

A third preparation of the title peroxide was carried out in a similar manner except that no diglyme safety diluent was employed. In this experiment 9.5 g (100% of theory, uncorrected; expected yield=9.5 g of undiluted product) of a slightly yellow liquid product was obtained. An IR spectrum of the product showed only a trace of an OH band in the 3500 $cm^{-1}$ region, a major monoperoxyoxalate carbonyl band at about 1795 $cm^{-1}$ and a major oxalate carbonyl band at about 1750 $cm^{-1}$. The product had a rapid heat test result of 51° C. which again confirmed that the product was a very low temperature peroxide.

Based on the method of preparation, crude yield data, rapid heat data and infrared spectral data, the desired peroxide product was prepared in this experiment.

EXAMPLE 3

Preparation of O-Ethyl OO-(3-Ethoxycarbonylcarbonyloxy-1,1-dimethylbutyl) Monoperoxyoxalate (I-1) from (I-2)

A 250 mL 3-necked flask equipped with a magnetic stirring bar, a condenser, a thermometer and an addition funnel and cooled with an ice bath was charged with 2.8 g (60 mmoles) of ethanol, 3.4 g (43 mmoles) of dry pyridine and 60 mL of MTBE. The flask contents were cooled to 0° C. Then to the resulting vigorously stirred solution at 0° C. was slowly added 4.8 g (15 mmoles) of 1,3-dimethyl-3-(chlorocarbonylcarbonylperoxy)butyl chlorooxalate (I-2) in 10 mL of MTBE. After the addition was completed the reaction mass was stirred for 60 minutes at 2° C. after which 20 mL of water is added and the reaction mass was stirred an additional 5 minutes at 3–4° C. The aqueous layer was then separated and the organic layer was washed three times with 35 mL portions of aqueous 5% HCl solution and then twice with 50 mL portions of water. The product solution was dried over 5% by weight of anhydrous $MgSO_4$, and, after separation of the spent desiccant by filtration, the solvent was removed in vacuo using a water aspirator/vacuum pump at 0° C. leaving 3.6 g (72% of theory, uncorrected) of a colorless liquid. An IR spectrum of the product showed a slight OH band in the 3500 $cm^{-1}$ region, a major monoperoxyoxalate carbonyl band at 1791.1 $cm^{-1}$ and a major oxalate carbonyl band was present at 1741.6 $cm^{-1}$. There was a peroxide (—OO—) band at about 860 $cm^{-1}$. The product had a rapid heat test result of 60° C. which confirmed that the product was a very low temperature peroxide.

Based on the method of preparation, yield data, rapid heat data and infrared spectral data the product obtained in this reaction was the desired title product, I-1. The IR spectrum of the product from this example was exactly the same as the IR spectrum of the product from Example 1. Hence, two different synthetic methods were used to prepare O-ethyl OO-(3-ethoxycarbonylcarbonyloxy-1,1-dimethylbutyl) monoperoxyoxalate, i.e., the method of this example and the method of Example 1.

EXAMPLE 4

Preparation of O-Ethyl OO-(3-Hydroxy-1,1-dimethylbutyl) Monoperoxyoxalate (I-3)

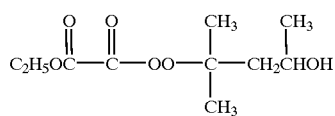
(I-3)

A 250 mL 3-necked flask equipped with a magnetic stirring bar, a condenser, a thermometer and an addition funnel and cooled with an dry ice bath was charged with 6.0 g (44.0 mmoles) of dry 98% 3-hydroxy-1,1-dimethylbutyl hydroperoxide, 9.8 g (80.0 mmoles) of dry 2,4,6-collidine and 50 mL of methylene chloride. The flask contents were cooled to −78° C. Then to the resulting vigorously stirred solution at −78° C. was slowly added a solution of 5.6 g (40.0 mmoles) of 98% ethyl oxalyl chloride in 40 mL of methylene chloride over a period of 15–20 minutes. After the addition was completed the reaction mass was stirred for 4 hours at −78° C., then for 60 minutes at 25° C., after which 100 mL of water was added and the reaction mass was stirred an additional 5 minutes at 25° C. The aqueous layer was then separated and the organic layer was washed two times with 50 mL portions of aqueous 5% HCl solution and then with 50 mL portions of water until the washes were neutral. The product solution was dried over 5% by weight of anhydrous $MgSO_4$, and, after separation of the spent desiccant by filtration, the solvent was removed in vacuo leaving 5.5 g (59% of theory, uncorrected) of a colorless oil. An IR spectrum of the product showed a large OH band in the 3500 $cm^{-1}$ region, a major monoperoxyoxalate carbonyl band at 1790 $cm^{-1}$ and a major oxalate carbonyl band at about 1735 $cm^{-1}$. The product had a rapid heat test result of 55° C. which confirmed that the product was a very low temperature peroxide. The product contained 3.71% active oxygen (theory, 6.83%) according to a peroxyester active oxygen method, therefore, the assay of the product was 54% and the corrected yield was 32%.

Based on the method of preparation, active oxygen content, rapid heat data and infrared spectral data the product obtained in this reaction was the desired title product.

EXAMPLE 5

Preparation of O-(2-Ethylhexyl) OO-(3-Hydroxy-1,1-dimethylbutyl) Monoperoxyoxalate (I-4)

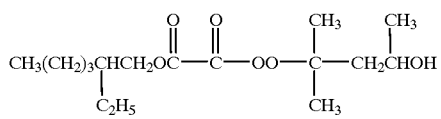
(I-4)

A 250 mL 3-necked flask equipped with a magnetic stirring bar, a condenser, a thermometer and an addition funnel and cooled with an dry ice bath was charged with 6.4 g (44.0 mmoles) of dry 92% 3-hydroxy-1,1-dimethylbutyl hydroperoxide, 9.8 g (80.0 mmoles) of dry 2,4,6-collidine and 50 mL of methylene chloride. The flask contents were cooled to −78° C. Then to the resulting vigorously stirred solution at −78° C. was slowly added a solution of 9.0 g (40.0 mmoles) of 98% 2-ethylhexyl oxalyl chloride (prepared by reacting excess oxalyl chloride with 2-ethylhexanol, followed by removal of excess oxalyl chloride) in 40 mL of methylene chloride over a period of 15–20 minutes. After the addition was completed the reaction mass was stirred for 4 hours at −78° C., then for 60 minutes at 25° C., after which 100 mL of water was added and the reaction mass was stirred an additional 5 minutes at 25° C. The aqueous layer was then separated and the organic layer was washed two times with 50 mL portions of aqueous 5% HCl solution and then with 50 mL portions of water until the washes were neutral. The product solution was dried over 5% by weight of anhydrous $MgSO_4$, and, after separation of the spent desiccant by filtration, the solvent was removed in vacuo leaving 10.0 g (79% of theory, uncorrected) of a colorless oil. An IR spectrum of the product showed a large OH band in the 3500 $cm^{-1}$ region. The product had a rapid heat test result of 58° C. which confirmed that the product was a low temperature peroxide. The product contained 3.98% active oxygen (theory, 5.02%) according to a peroxyester active oxygen method, therefore, the assay of the product was 79% and the corrected yield was 62%.

Based on the method of preparation, yield data, rapid heat data and infrared spectral data the product obtained in this reaction was the desired title product.

EXAMPLE 6

Preparation of O-(2-Ethylhexyl) OO-[3-(2-Ethylhexoxycarbonylcarbonyloxy)-1,1-dimethylbutyl] Monoperoxyoxalate (I-5)

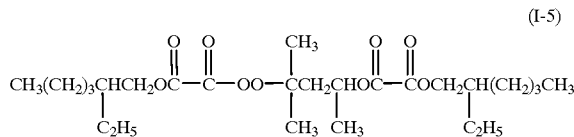

A jacketed, open-top reactor (ca. 250 mL) equipped with a mechanical stirrer, a thermometer and an addition funnel and cooled with circulating ice water was charged with 2.9 g (20 mmoles) of dry 91.7% 3-hydroxy-1,1-dimethylbutyl hydroperoxide, 3.5 g (44 mmoles) of dry pyridine and 75 mL of methylene chloride. The flask contents were cooled to 0° C. Then to the resulting vigorously stirred solution at about 0° C. was slowly added a solution of 8.8 g (40 mmoles) of 98% 2-ethylhexyl chlorooxalate (previously prepared by reacting excess oxalyl chloride with 2-ethylhexanol, followed by removal of excess oxalyl chloride) in 25 mL of methylene chloride. After the addition was finished, the reaction mass was stirred for 60 minutes at 0° C. after which 50 mL of water was added and the reaction mass was stirred an additional 10 minutes at 5° C. The aqueous layer was then separated and the organic layer washed with a 20 mL portion of aqueous 5% HCl solution and then twice with 50 mL portions of water. The product solution was dried over about 5% by weight of anhydrous MgSO$_4$, and, after separation of the spent desiccant by filtration, the solvent was removed in vacuo leaving 10.5 g (>100% of theory, uncorrected) of a colorless liquid. An IR spectrum of the product showed a major monoperoxyoxalate carbonyl band at about 1790 cm$^{-1}$ and an oxalate carbonyl band at about 1750 cm$^{-1}$. The product had a rapid heat test result of 72–75° C. which confirmed that the product was a very low temperature peroxide. The product contained 2.86% active oxygen (theory, 3.18%) according to a peroxyester active oxygen method, therefore, the assay of the product was 90% and the corrected yield was 94%.

Based on the method of preparation, yield data, rapid heat data and infrared spectral data the product obtained in this reaction was the desired title product.

EXAMPLE 7

Preparation of OO-[3-(4-Methyl-2-pentoxycarbonylcarbonyloxy)-1,1-dimethylbutyl] O-(4-Methyl-2-pentyl) Monoperoxyoxalate (I-6)

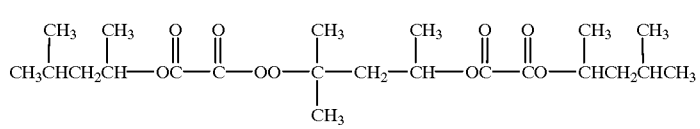

In this example the product was prepared in two synthetic steps. In the first step 4-methyl-2-pentanol was reacted with 50% molar excess of oxalyl chloride. Upon completion of the reaction the excess oxalyl chloride was stripped from the product at reduced pressure to produce 4-methyl-2-pentyl chlorooxalate having an assay of 96.2% and in a corrected yield of 88.2%. In the second step 4-methyl-2-pentyl chlorooxalate was reacted with 3-hydroxy-1,1-dimethylbutyl hydroperoxide in the presence of pyridine to yield the product as described below:

A 250 mL 3-necked flask equipped with a magnetic stirring bar, a condenser, a thermometer and an addition funnel and cooled with an ice bath was charged with 4.3 g (30.0 mmoles) of dry 94.4% 3-hydroxy-1,1-dimethylbutyl hydroperoxide, 6.7 g (85.0 mmoles) of dry pyridine and 50 mL of methyl t-butyl ether (MTBE). The flask contents were cooled to 3° C. Then to the resulting vigorously stirred solution at 3–8° C. was slowly added a solution of 11.9 g (59.4 mmoles) of 96.2% 4-methyl-2-pentyl chlorooxalate in 25 mL of MTBE over a period of 30 minutes. The reaction mass was stirred for 60 minutes at 0–5° C. after which it was washed with 100 mL of water, two 50-mL portions of aqueous 5% hydrochloric acid solution and to a pH of 7 with 100 mL portions of water. The product solution was dried over 5% by weight of anhydrous MgSO$_4$, and, after separation of the spent desiccant by filtration, the solvent was removed in vacuo leaving 12.6 g (95% of theory, uncorrected) of a colorless liquid. An IR spectrum of the product showed no significant OH band in the 3500 cm$^{-1}$ region. A major monoperoxyoxalate carbonyl band was present at 1795 cm$^{-1}$ and a major oxalate carbonyl band was present at about 1740 cm$^{-1}$. The product had a rapid heat test result of 48° C. which confirmed that the product was a very low temperature peroxide.

Based on the method of preparation, yield data, rapid heat data and infrared spectral data the product obtained in this reaction was the desired title product.

EXAMPLE 8

Preparation of O-t-Butyl OO-(3-t-Butoxycarbonylcarbonyloxy)-1,1-dimethylbutyl] Monoperoxyoxalate (I-7)

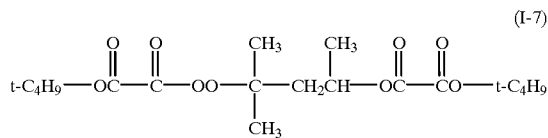

A 250 mL 3-necked flask equipped with a magnetic stirring bar, a condenser, a thermometer and an addition funnel and cooled with an ice bath was charged with 4.3 g (30.0 mmoles) of dry 94.4% 3-hydroxy-1,1-dimethylbutyl hydroperoxide, 6.7 g (85.0 mmoles) of dry pyridine and 60 mL of MTBE. The flask contents were cooled to 0° C. Then to the resulting vigorously stirred solution at 5–8° C. was slowly added a solution of 10.4 g (63.0 mmoles) of 100% t-butyl chlorooxalate (previously prepared by reacting excess oxalyl chloride with t-butanol, followed by removal of excess oxalyl chloride) in 10 mL of MTBE. After the addition was completed the reaction mass was stirred for 45 minutes at 0° C. after which 10 mL of water was added and the reaction mass was stirred an additional 20 minutes at 3–4° C. The aqueous layer was then separated and the organic layer was washed three times with 35 mL portions of aqueous 5% HCl solution and then twice with 75 mL portions of water. The product solution was dried over 5% by weight of anhydrous $MgSO_4$, and, after separation of the spent desiccant by filtration, the solvent was removed in vacuo leaving 11.0 g (94% of theory, uncorrected) of a colorless liquid. An IR spectrum of the product showed no significant OH band in the 3500 $cm^{-1}$ region. A major monoperoxyoxalate carbonyl band was present at 1790 $cm^{-1}$ and an oxalate carbonyl band was present at about 1735 $cm^{-1}$. The product had a very low rapid heat test result (36° C.) which confirmed that the product was a very low temperature peroxide.

Based on the method of preparation, yield data, rapid heat data and infrared spectral data the product obtained in this reaction was the desired title product.

EXAMPLE 9

Preparation of O-Neopentyl OO-(3-Neopentoxycarbonylcarbonyloxy-1,1-dimethylbutyl) Monoperoxyoxalate (I-8)

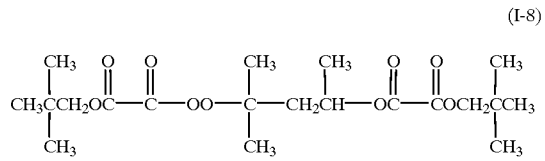

(I-8)

A 250 mL 3-necked flask equipped with a magnetic stirring bar, a condenser, a thermometer and an addition funnel and cooled with an ice bath was charged with 2.9 g (20 mmoles) of dry 94.4% 3-hydroxy-1,1-dimethylbutyl hydroperoxide, 4.5 g (57 mmoles) of dry pyridine and 60 mL of MTBE. The flask contents were cooled to 0° C. Then to the resulting vigorously stirred solution at about 0° C. was slowly added a solution of 7.5 g (42 mmoles) of 100% neopentyl chlorooxalate (previously prepared by reacting excess oxalyl chloride with neopentyl alcohol, followed by removal of excess oxalyl chloride) in 10 mL of MTBE. After the addition was finished, the reaction mass was stirred for 45 minutes at 0° C. after which 10 mL of water was added and the reaction mass was stirred an additional 20 minutes at 3–4° C. The aqueous layer was then separated and the organic layer washed three times with 35 mL portions of aqueous 5% HCl solution and then twice with 75 mL portions of water. The product solution was dried over 5% by weight of anhydrous $MgSO_4$, and, after separation of the spent desiccant by filtration, the solvent was removed in vacuo leaving 9.0 g (>100% of theory, uncorrected) of a colorless liquid. An IR spectrum of the product showed a small OH band in the 3500 $cm^{-1}$ region. A major monoperoxyoxalate carbonyl band was present at about 1790 $cm^{-1}$ and an oxalate carbonyl band was present at about 1735 $cm^{-1}$. The product had a rapid heat test result of 75° C. which confirmed that the product was a very low temperature peroxide. The product contained 3.61% active oxygen (theory, 3.82%) according to a peroxyester active oxygen method, therefore, the assay of the product was 95% and the corrected yield was 100%.

Based on the method of preparation, yield data, rapid heat data and infrared spectral data the product obtained in this reaction was the desired title product.

EXAMPLE 10

Preparation of O-Benzyl OO-(3-Benzyloxycarbonylcarbonyloxy-1,1-dimethylbutyl) Monoperoxyoxalate (I-9)

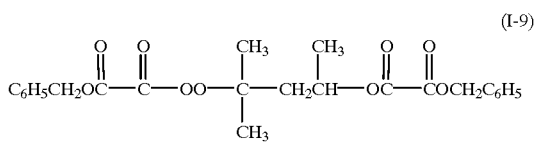

(I-9)

A 250 mL 3-necked flask equipped with a magnetic stirring bar, a condenser, a thermometer and an addition funnel and cooled with an ice bath was charged with 2.9 g (20 mmoles) of dry 94.4% 3-hydroxy-1,1-dimethylbutyl hydroperoxide, 4.5 g (57 mmoles) of dry pyridine and 60 mL of MTBE. The flask contents were cooled to 1° C. Then to the resulting vigorously stirred solution at about 0° C. was slowly added a solution of 8.6 g (42 mmoles) of 96.6% benzyl chlorooxalate (previously prepared by reacting excess oxalyl chloride with benzyl alcohol, followed by removal of excess oxalyl chloride) in 10 mL of MTBE. After the addition was finished, the reaction mass was stirred for 45 minutes at 2° C. after which 10 mL of water was added and the reaction mass was stirred an additional 20 minutes at 3–4° C. The aqueous layer was then separated and the organic layer washed three times with 35 mL portions of aqueous 5 HCl solution and then twice with 75 mL portions of water. The product solution was dried over by weight of anhydrous $MgSO_4$, and, after separation of the spent desiccant by filtration, the solvent was removed in vacuo leaving 9.1 g (99% of theory, uncorrected) of a colorless liquid. An IR spectrum of the product showed a slight OH band in the 3500 $cm^{-1}$ region. A major monoperoxyoxalate carbonyl band was present at 1790 $cm^{-1}$ and an oxalate carbonyl band was present at about 1740 $cm^{-1}$. The product had a rapid heat test result of 73° C. which confirmed that the product was a very low temperature peroxide. The product contained 3.02% active oxygen (theory, 3.49%) according to a peroxyester active oxygen method, therefore, the assay of the product was 87% and the corrected yield was 86%.

Based on the method of preparation, yield data, rapid heat data and infrared spectral data the product obtained in this reaction was the desired title product.

EXAMPLE 11

Preparation of O-Hexafluoroamyl OO-(3-Hexafluoroamyloxycarbonylcarbonyloxy-1,1-dimethylbutyl) Monoperoxyoxalate (I-10)

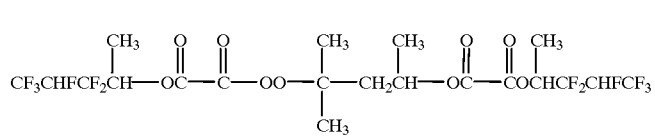

(I-10)

A 250 mL 3-necked flask equipped with a magnetic stirring bar, a condenser, a thermometer and an addition funnel and cooled with an ice bath was charged with 1.5 g (10 mmoles) of dry 94.4% 3-hydroxy-1,1-dimethylbutyl hydroperoxide, 2.3 g (29 mmoles) of dry pyridine and 60 mL of MTBE. The flask contents were cooled to 1° C. Then to the resulting vigorously stirred solution at about 0° C. was slowly added a solution of 6.6 g (21 mmoles) of 91.3% hexafluoroamyl chlorooxalate (previously prepared by reacting excess oxalyl chloride with hexafluoroamyl alcohol, followed by removal of excess oxalyl chloride) in 10 mL of MTBE. After the addition was finished, the reaction mass was stirred for 45 minutes at 0° C. after which 10 mL of water was added and the reaction mass was stirred an additional 20 minutes at 3–4° C. The aqueous layer was then separated and the organic layer washed three times with 35 mL portions of aqueous 5% HCl solution and then twice with 75 mL portions of water. The product solution was dried over 5% by weight of anhydrous $MgSO_4$, and, after separation of the spent desiccant by filtration, the solvent was removed in vacuo leaving 7.3 g (>100% of theory, uncorrected) of a colorless liquid. The product contained 1.77% active oxygen (theory, 2.52%) according to a peroxyester active oxygen method, therefore, the assay of the product was 70% and the corrected yield was 81%. The product had a rapid heat test result of 93° C. which confirmed that the product was a low temperature peroxide. The higher rapid heat temperature compared to other similar monoperoxyoxalates was due to the lower active oxygen content of the product compared to those of other monoperoxyoxalates.

Based on the method of preparation, yield data, rapid heat data and infrared spectral data the product obtained in this example was the desired title product.

EXAMPLE 12

Preparation of OO-[3-(3-t-Butylperoxy-1,3-dimethylbutoxycarbonylcarbonyloxy)-1,1-dimethylbutyl] O-(3-t-Butylperoxy-1,3-dimethylbutyl) Monoperoxyoxalate (I-11)

In this example the product was prepared in two synthetic steps. In the first step 3-t-butylperoxy-1,3-dimethylbutanol was reacted with 100% molar excess of oxalyl chloride. Upon completion of the reaction the excess oxalyl chloride was stripped from the product at reduced pressure to produce 3-t-butylperoxy-1,3-dimethylbutyl chlorooxalate having an assay of 98.1% and in a corrected yield of 98.4%. In the second step 3-t-butylperoxy-1,3-dimethylbutyl chlorooxalate was reacted with 3-hydroperoxy-1,3-dimethylbutanol in the presence of pyridine to yield the product as described below:

A 250 mL 3-necked flask equipped with a magnetic stirring bar, a condenser, a thermometer and an addition funnel and cooled with an ice bath was charged with 2.9 g (20.0 mmoles) of dry 94.1% 3-hydroxy-1,1-dimethylbutyl hydroperoxide, 4.8 g (61.0 mmoles) of dry pyridine and 40 mL of MTBE. The flask contents were cooled to 3° C. Then to the resulting vigorously stirred solution at 3–7° C. was slowly added a solution of 11.5 g (40.0 mmoles) of 98.1% 3-t-butylperoxy-1,3-dimethylbutyl chlorooxalate in 10 mL of MTBE over a period of 30 minutes. The reaction mass was stirred for 120 minutes at 0–10° C. after which it was washed with 100 mL of water, two 50-mL portions of aqueous 5% hydrochloric acid solution and to a pH of 7 with 100 mL portions of water. The product solution was dried over 5% by weight of anhydrous $MgSO_4$, and, after separation of the spent desiccant by filtration, the solvent was removed in vacuo leaving 12.1 g (97% of theory, uncorrected) of a colorless liquid. An IR spectrum of the product showed no significant OH band in the 3500 $cm^{-1}$ region. A major monoperoxyoxalate carbonyl band was present at about 1800 $cm^{-1}$ and a major oxalate carbonyl band was present at about 1750 $cm^{-1}$. Based on monoperoxyoxalate active oxygen content (2.08%) the assay of the product was about 80% and the corrected yield was about 78%.

Based on the method of preparation, assay and yield data, and infrared spectral data the product obtained in this reaction was the desired title product.

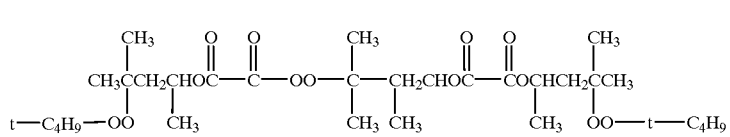

(I-11)

EXAMPLE 13

Preparation of t-Butyl 3-t-Butylperoxycarbonylcarbonyloxy-1,1-dimethylbutyl Diperoxyoxalate (I-12)

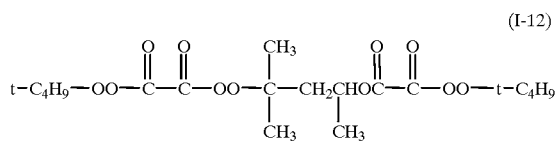

(I-12)

In this example the product was prepared in two synthetic steps. In the first step t-butyl hydroperoxide was reacted with 100% molar excess of oxalyl chloride to form t-butylperoxy chlorooxalate (A-1).

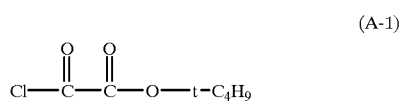

(A-1)

In the second step t-butylperoxy chlorooxalate (A-1) was reacted with 3-hydroxy-1,1-dimethylbutyl hydroperoxide in the presence of pyridine to yield the product (I-12).

A 125 mL flask was charged with 9.3 g (100 mmoles) of 97% t-butyl hydroperoxide, 75 mL of pentane and 3 g of anhydrous $MgSO_4$ at room temperature. The contents were stirred for 30 minutes after which the contents were filtered and the spent dessicant was washed with 25 mL of pentane and the pentane washings were combined with the filtrate. A 3-neck flask equipped with a magnetic stirring bar, a condenser, a thermometer and an addition funnel and cooled with a ice-water bath was then charged with 25.4 g (200 mmoles) of oxalyl chloride and 25 mL of pentane. The solution was cooled to 0° C. Then the dry pentane solution of t-butyl hydroperoxide was added slowly to the stirred oxalyl chloride/pentane solution over a period of 60 minutes at 0° C. The reaction was stirred for an additional 3 hours at 0° C. Then the pentane and excess oxalyl chloride were removed by stripping at ice-water temperature, leaving 18.5 g (>100% of theory, uncorrected; theoretical yield=18.1 g) of a liquid product. An IR spectrum of the product showed a very slight OH band in the 3500 cm$^{-1}$ region and a single, major monoperoxyoxalate carbonyl band at 1797 cm$^{-1}$. The product had a rapid heat test result of 45° C. (very loud pop) which confirmed that the product, t-butylperoxy chlorooxalate, was a very low temperature peroxide. Impact shock testing [J. Chem. Ed. 48, A 451 (1971)] showed that the product was shock sensitive at 3 inches and not shock sensitive at one inch. Because of the product's thermal and shock sensitivities, it was diluted with an equal weight of diglyme prior to subsequent use. The diglyme-diluted product had a rapid heat test result of 60° C. (mild decomposition) and a shock sensitivity above 20 inches.

In the second step, a 250 mL 3-necked flask equipped with a magnetic stirring bar, a condenser, a thermometer and an addition funnel and cooled with an ice bath was charged with 1.4 g (10.0 mmoles) of dry 94.4% 3-hydroxy-1,1-dimethylbutyl hydroperoxide, 2.3 g (29.0 mmoles) of dry pyridine and 60 mL of MTBE. The flask contents were cooled to 0° C. Then to the resulting vigorously stirred solution at 0° C. was slowly added a solution of 7.7 g (21.0 mmoles) of about a 50% diglyme solution of t-butylperoxy chlorooxalate in 10 mL of MTBE. After the addition was completed the reaction mass was stirred for 60 minutes at 0° C. after which 10 mL of water was added and the reaction mass was stirred an additional 20 minutes at 0° C. The aqueous layer was then separated and the organic layer was washed three times with 35 mL portions of aqueous 5% HCl solution and then twice with 75 mL portions of aqueous 5% $NaHCO_3$ solution. The product solution was dried over 5% by weight of anhydrous $MgSO_4$, and, after separation of the spent desiccant by filtration, the solvent was removed in vacuo leaving 3.9 g (91% of theory, uncorrected; theoretical yield=4.3 g) of a colorless liquid. An IR spectrum of the product showed a slight OH band in the 3500 cm$^{-1}$ region, a major peroxyoxalate carbonyl band was present at 1797 cm$^{-1}$, an oxalate carbonyl band was present at about 1750 cm$^{-1}$ and a peroxide (—OO—) band was present at about 845 cm$^{-1}$. Impact shock testing showed that the product was shock sensitive at 3 inches and not shock sensitive at one inch. The product was diluted with an equal weight of diglyme (to about 50% active) in order to suppress the product's impact shock sensitivity. The diglyme-diluted product had a shock sensitivity above 20 inches and a rapid heat test result of 45–48° C. The latter result confirmed that the product was an extremely low temperature peroxide.

Based on the method of preparation, yield data, rapid heat data and infrared spectral data the product obtained in this reaction was the desired title product.

EXAMPLE 14

Polymerization of Methyl Methacrylate Using OO-[3-(4-Methyl-2-pentoxycarbonylcarbonyloxy)-1,1-dimethylbutyl] O-(4-Methyl-2-pentyl) Monoperoxyoxalate (I-6) as an Initiator A 250 mL 3-necked flask equipped with a magnetic stirring bar, a condenser and a thermometer was charged with 75 g of methyl ethyl ketone (MEK) and 30 g of methyl methacrylate (MMA). To the resulting vigorously stirred solution at 53–56° C. was slowly added a solution of 2.4 g (ca. 5.0 mmoles) of OO-[3-(4-methyl-2-pentoxycarbonylcarbonyloxy)-1,1-dimethylbutyl] O-(4-methyl-2-pentyl) monoperoxyoxalate (I-6) in 25 mL of MEK over a period of about 30 minutes. The reaction mass was stirred for 15 minutes at 55° C. and then for about 120 minutes at 65–70° C. The polymer solution was then cooled to about 30° C. and was poured into about 1500 mL of vigorously stirred water to precipitate the poly(methyl methacrylate) (PMMA). The slurry was allowed to stand overnight after which the solid PMMA was separated by filtration and air dried for 3 hours at 20–25° C. The polymer was washed with 50 mL of pentane, filtered and dried. Obtained was 11.3 g of PMMA polymer (ca. 35% of theory, uncorrected).

This example showed that a novel monoperoxyoxalate composition of this invention was an effective free-radical initiators for polymerizing ethylenically unsaturated monomers such as MMA.

EXAMPLE 15

Preparation of Methyl Methacrylate Polymer with Peroxide End-Groups Using OO-[3-(3-t-Butylperoxy-1,3-dimethylbutoxycarbonylcarbonyloxy)-1,1-dimethylbutyl] O-(3-t-Butyl-peroxy-1,3-dimethylbutyl) Monoperoxyoxalate (I-11) as an Initiator A 250 mL 3-necked flask equipped with a magnetic stirring bar, a condenser and a thermometer was charged with 75 g of MEK and 30 g of MMA. To the resulting vigorously stirred solution at 53–56° C. was slowly added a solution of 4.0 g (ca. 5.1 mmoles) of OO-[3-(3-t-butylperoxy-1,3-dimethylbutoxycarbonylcarbonyloxy)-1,1-dimethylbutyl] O-(3-t-butylperoxy-1,3-dimethylbutyl) monoperoxyoxalate (I-11) in 25 mL of MEK over a period of about 30 minutes. The reaction mass was stirred for 15 minutes at 55° C. and then for about 120 minutes at 65–70° C. The polymer solution was then cooled to about 30° C. and was poured into about 1500 mL of vigorously stirred water to precipitate the PMMA. The slurry was allowed to stand overnight after which the solid PMMA was separated by filtration and air dried for 2–3 hours at 20–25° C. The polymer was washed with 50 mL of pentane, filtered and dried. Obtained was 12.8 g of PMMA polymer (ca. 39% of theory, uncorrected) possessing peroxide end-groups. Analysis of the product by differential scanning calorimetry (DSC) showed a major peroxide decomposition exotherm at about 190° C. which confirmed the presence of peroxide groups covalently bonded at the ends of the polymer chains. The peroxy polymer was found to have molecular weights and molecular weight distribution as follows:

| | |
|---|---|
| $\overline{M}_n$ | 4,000 |
| $\overline{M}_w$ | 6,000 |
| $\overline{M}_z$ | 11,000 |

This example showed that a novel monoperoxyoxalate composition of this invention was an effective free-radical initiators for polymerizing ethylenically unsaturated monomers such as MMA.

EXAMPLE 16

140° F. (60° C.) SPI Exotherm Data for O-Ethyl OO-(3-Ethoxycarbonylcarbonyloxy-1,1-dimethylbutyl) Monoperoxyoxalate (I-1)

The unsaturated polyester resin composition employed in this example was a mixture of an unsaturated polyester and styrene monomer. The unsaturated polyester was an alkyd resin made by esterifying the following components:

| COMPONENT | QUANTITY (MOLES) |
|---|---|
| Maleic Anhydride | 1.0 |
| Phthalic Anhydride | 1.0 |
| Propylene Glycol | 2.2 |

0.013% by weight of hydroquinone inhibitor was added to the resulting resin. The alkyd resin had an Acid No. of 45–50. Seven (7) parts by weight of the above unsaturated polyester alkyd resin were diluted with three (3) parts by weight of styrene monomer. The resulting unsaturated polyester resin composition had the following properties:

| | |
|---|---|
| Viscosity (Brookfield No. 2 at 20 r. p. m.) | 13.0 poise |
| Specific Gravity | 1.14 |

Gelation and cure characteristics of di(4-t-butylcyclohexyl) peroxydicarbonate (A-1), (a commercial peroxide product used to cure unsaturated polyester resin compositions), t-butyl peroxyneodecanoate (A-2), (another commercial peroxide product used to cure unsaturated polyester resin compositions), α-cumyl peroxyneodecanoate (A-3) (a commercial low temperature peroxide initiator) and O-ethyl OO-(3-ethoxycarbonylcarbonyloxy-1,1-dimethylbutyl) monoperoxyoxalate (I-1), a novel monoperoxyoxalate composition of the instant invention, were determined using the Standard SPI Exotherm Procedure (Suggested SPI Procedure for Running Exotherm Curves—Polyester Resins, published in the Preprint of the 24th Annual Technical Conference—Reinforced Plastics/Composites Division, Society of the Plastics Industry, Inc., 1969). Using this procedure at 140° F. (60° C.), A-1, A-2, A-3 and I-1 were comparatively evaluated. The level of I-1 was 1.0 g per 100 g of resin on a pure basis and the levels of A-1, A-2 and A-3 (per 100 g of resin) were equivalent in active oxygen content to a 1.0 g level of I-1 (pure basis). The results of this investigation are given in Example 16 Table and show that I-1 gelled and cured the resin much more rapidly than A-1, A-2 and A-3, hence, I-1, a novel monoperoxyoxalate composition of the instant invention, was much more active in curing the unsaturated polyester resin than were three of the lowest temperature, commercial peroxide catalysts.

EXAMPLE 16 TABLE
140° F. (60° C.) SPI EXOTHERM DATA

| CURING AGENT | G/100 G RESIN | GEL, MINS. | CURE, MINS. | PEAK EXO, ° F. | BARCOL HARDNESS |
|---|---|---|---|---|---|
| I-1 | 1.0 | 2.0 | 3.3 | 326 | 40–43 |
| A-1 | 1.21 | 9.0 | 11.4 | 296 | 35–40 |
| A-2 | 0.73 | 11.9 | 15.0 | 310 | 35–40 |
| A-3 | 0.92 | 5.2 | 7.2 | 304 | 30–32 |

The subject matter regarded by the applicant as their invention is particularly pointed out and distinctly claimed as follows:

We claim:

1. Peroxyoxalates of Structure A:

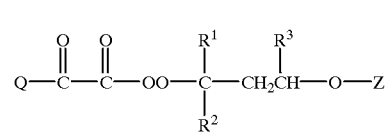

where

R¹, R² and R³ are alkyl radicals of 1 to 4 carbons, and, additionally, R³ can be hydrogen, and, Q is selected from the group consisting of chloro, bromo, R—O, and R⁴—OO, where R is selected from the group consisting of H, a substituted or unsubstituted alkyl radical of 1 to 24 carbons, substituents being one or more alkyl radicals of 1 to 6 carbons, alkoxy radicals of 1 to 6 carbons, aryloxy radicals of 6–10 carbons, fluoro, chloro, bromo, carboxy and cyano, a substituted or unsubstituted alkenyl radical of 3 to 12 carbons, substituents being one or more lower alkyl radicals of 1 to 4 carbons, a substituted or unsubstituted aryl radical of 6 to 10 carbons, substituents being one or more alkyl radicals of 1 to 6 carbons, alkoxy radicals of 1 to 6 carbons, aryloxy radicals of 6 to 10 carbons, chloro, bromo and cyano, a substituted or unsubstituted aralkyl radical of 7 to 13 carbons, substituents being one or more alkyl radicals of 1 to 6 carbons, a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, a substituted or unsubstituted bicycloalkyl radical of 6 to 14 carbons, with substituents being one or more lower alkyl radicals of 1 to 4 carbons, and, R- can additionally be structure (a),

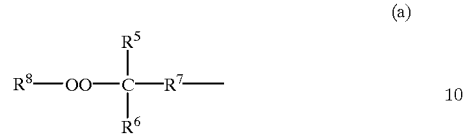

(a)

where

R$^5$ and R$^6$ are alkyl radicals of 1 to 4 carbons, R$^7$ is an unsubstituted alkylene diradical of 1 to 3 carbons or a substituted alkylene diradical of 1 to 3 carbons, substituents being one or more lower alkyl radicals of 1 to 4 carbons, R$^8$ is selected from unsubstituted t-alkyl radicals of 4 to 12 carbons, substituted t-alkyl radicals of 4 to 12 carbons, t-cycloalkyl radicals of 6 to 13 carbons, t-alkynyl radicals of 5 to 9 carbons, t-aralkyl radicals of 9 to 13 carbons, unsubstituted aroyl radicals of 7 to 11 carbons, substituted aroyl radicals of 7 to 11 carbons, where the substituent for the t-alkyl radicals is a t-alkylperoxy radical of 4 to 8 carbons and the substituents for the aroyl radicals are one or more lower alkyl radicals of 1 to 4 carbons, alkoxy radicals of 1 to 4 carbons, phenyl radicals, acyloxy radicals of 2 to 8 carbons, t-alkylperoxycarbonyl radicals of 5 to 9 carbons, fluoro, chloro or bromo, and R$^8$ can also be structures (b), (c) and (d)

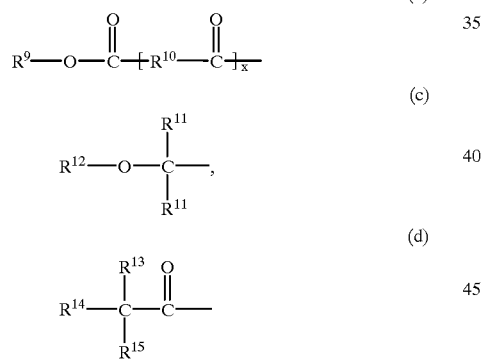

where x is 0 or 1, R$^9$ is a substituted or unsubstituted alkyl radical of 1 to 18 carbons, substituents being one or more alkyl radicals of 1 to 6 carbons, t-alkylperoxy radicals of 4 to 8 carbons, alkoxy radicals of 1 to 6 carbons, aryloxy radicals of 6 to 10 carbons, hydroxy, chloro, bromo or cyano or a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, and, R$^{10}$ is selected from a substituted or unsubstituted alkylene diradical of 2 to 3 carbons, substituents being one or more lower alkyl radicals of 1 to 4 carbons, or a substituted or unsubstituted 1,2-, 1,3- or 1,4-phenylene diradical, substituents being one or more lower alkyl radicals of 1 to 4 carbons, chloro, bromo, nitro or carboxy, and, R$^{11}$ is a lower alkyl radical of 1 to 4 carbons, and, additionally, the two R$^{11}$ radicals may be concatenated to form an alkylene diradical of 4 to 5 carbons, R$^{12}$ is a lower alkyl radical of 1 to 4 carbons, R$^{13}$, R$^{14}$ and R$^{15}$ are selected from hydrogens, alkyl radicals of 1 to 8 carbons, aryl radicals of 6 to 10 carbons, alkoxy radicals of 1 to 8 carbons and aryloxy radicals of 6 to 10 carbons, and, R$^4$ is selected from an unsubstituted t-alkyl radical of 4 to 12 carbons, a substituted t-alkyl radical of 4 to 12 carbons, a t-cycloalkyl radical of 6 to 13 carbons, a t-alkynyl radical of 5 to 9 carbons, and a t-aralkyl radical of 9 to 13 carbons, where the substituent for the t-alkyl radical is a t-alkylperoxy radical of 4 to 8 carbons and, Z is selected from the group consisting of hydrogen and structures (e), (f) and (g),

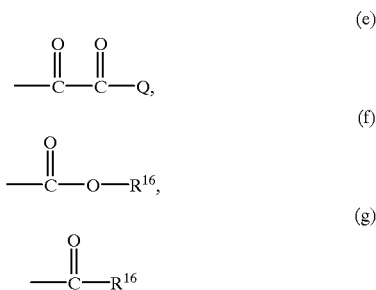

where R$^{16}$ is selected from the group consisting of a substituted or unsubstituted alkyl radical of 1 to 24 carbons, substituents being one or more alkyl radicals of 1 to 6 carbons, alkoxy radicals of 1 to 6 carbons, aryloxy radicals of 6 to 10 carbons, chloro, bromo, carboxy and cyano, a substituted or unsubstituted alkenyl radical of 3 to 12 carbons, substituents being one or more lower alkyl radicals of 1 to 4 carbons, a substituted or unsubstituted aryl radical of 6 to 10 carbons, substituents being one or more alkyl radicals of 1 to 6 carbons, alkoxy radicals of 1 to 6 carbons, aryloxy radicals of 6 to 10 carbons, chloro, bromo and cyano, a substituted or unsubstituted aralkyl radical of 7 to 13 carbons, substituents being one or more alkyl radicals of 1 to 6 carbons, a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, and a substituted or unsubstituted bicycloalkyl radical of 6 to 10 carbons, with substituents being one or more lower alkyl radicals of 1 to 4 carbons.

2. Peroxyoxalates as defined in claim 1 wherein R is selected from the group consisting of H, a substituted or unsubstituted alkyl radical of 1 to 18 carbons, substituents being one or more alkyl radicals of 1 to 6 carbons, alkoxy radicals of 1 to 6 carbons, aryloxy radicals of 6 to 10 carbons, fluoro, chloro, bromo, carboxy and cyano, a substituted or unsubstituted aralkyl radical of 7 to 13 carbons, substituents being one or more alkyl radicals of 1 to 6 carbons, a substituted or unsubstituted cycloalkyl radical of 5 to 12 carbons, substituents being one or more lower alkyl radicals of 1 to 4 carbons, and structure (a).

3. Peroxyoxalates as defined in claim 1 wherein R is selected from the group consisting of H, a substituted or unsubstituted alkyl radical of 1 to 18 carbons, substituents being one or more alkyl radicals of 1 to 6 carbons, alkoxy radicals of 1 to 6 carbons, aryloxy radicals of 6 to 10 carbons, fluoro, chloro, bromo, carboxy and cyano, a substituted or unsubstituted cycloalkyl radical of 5 to 12 carbons, substituents being one or more lower alkyl radicals of 1 to 4 carbons, and structure (a).

4. A monoperoxyoxalate as defined in claim 1 selected from the group consisting of:

O-ethyl OO-(3-ethoxycarbonylcarbonyloxy-1,1-dimethylbutyl) monoperoxyoxalate,

OO-[3-(4-methyl-2-pentoxycarbonylcarbonyloxy)-1,1-dimethylbutyl] O-(4-methyl-2-pentyl) monoperoxyoxalate, OO-[3-(3-t-butylperoxy-1,3-dimethylbutoxycarbonylcarbonyloxy)-1,1-dimethylbutyl] O-(3-t-butylperoxy-1,3-dimethylbutyl) monoperoxyoxalate, 1,3-dimethyl-3-(chlorocarbonylcarbonylperoxy)butyl chlorooxalate, O-ethyl OO-(3-hydroxy-1,1-dimethylbutyl) monoperoxyoxalate, O-(2-ethylhexyl) OO-(3-hydroxy-1,1-dimethylbutyl) monoperoxyoxalate, O-(2-ethylhexyl) OO-[3-(2-ethylhexoycarbonylcarbonyloxy)-1,1-dimethylbutyl] monoperoxyoxalate, O-t-butyl OO-(3-t-butoxycarbonylcarbonyloxy)-1,1-dimethylbutyl] monoperoxyoxalate, O-neopentyl OO-(3-neopentoxycarbonylcarbonyloxy-1,1-dimethylbutyl) monoperoxyoxalate, O-benzyl OO-(3-benzyloxycarbonylcarbonyloxy-1,1-dimethylbutyl) monoperoxyoxalate, O-hexafluoroamyl OO-(3-hexafluoroamyloxycarbonylcarbonyloxy-1,1-dimethylbutyl) monoperoxyoxalate, and t-butyl 3-t-butylperoxycarbonylcarbonyloxy-1,1-dimethylbutyl diperoxyoxalate.

5. A monoperoxyoxalate as defined in claim 1 wherein Z is structure (e).

6. A monoperoxyoxalate as defined in claim 1 wherein Z is hydrogen.

7. A process for use of the monoperoxyoxalates as defined in claim 1 as free-radical initiators for the curing of unsaturated polyester resin compositions by heating such resins in the presence of initiating amounts of the novel peroxide compositions of claim 1 at appropriate temperatures.

8. A process for the polymerization of ethylenically unsaturated monomers which comprises treating such monomers with initiating amounts of the monoperoxyoxalates defined in claim 1 at temperatures of from 0° C. to 100° C.

* * * * *